(12) United States Patent
Ko et al.

(10) Patent No.: US 9,758,595 B2
(45) Date of Patent: Sep. 12, 2017

(54) **METHOD TO PREPARE *GANODERMA LUCIDUM* POLYSACCHARIDES POSSESSING ANTI-OBESITY PROPERTIES AND USES THEREOF**

(71) Applicant: Chang Gung Biotechnology Corp., Taipei (TW)

(72) Inventors: Yun-Fei Ko, Taipei (TW); Jan Martel, Taipei (TW); Jian-Ching Liau, Taipei (TW); I-Te Chang, Taipei (TW); Wei-Ting Jian, Taipei (TW); Mei-Feng Lin, Taipei (TW); Chia-Jen Yang, Taipei (TW); Chen-Yaw Chiu, Taipei (TW); Chih-Jung Chang, Taipei (TW); Chuan-Sheng Lin, Taipei (TW); Tsung-Ru Wu, Taipei (TW); Chia-Chen Lu, Taipei (TW); David Marcelo Ojcius, Taipei (TW); Hsin-Chih Lai, Taipei (TW); John D. Young, Taipei (TW)

(73) Assignee: Chang Gung Biotechnology Corp., Taipei (TW)

( * ) Notice: Subject to any disclaimer, the term of this patent is extended or adjusted under 35 U.S.C. 154(b) by 13 days.

(21) Appl. No.: 14/854,901

(22) Filed: Sep. 15, 2015

(65) Prior Publication Data
US 2016/0347867 A1    Dec. 1, 2016

(30) Foreign Application Priority Data
May 25, 2015 (TW) .............................. 104116656 A

(51) Int. Cl.
*A61K 31/715* (2006.01)
*A61K 36/074* (2006.01)
*C08B 37/00* (2006.01)

(52) U.S. Cl.
CPC .......... *C08B 37/006* (2013.01); *A61K 31/715* (2013.01); *A61K 36/074* (2013.01); *C08B 37/0003* (2013.01); *A61K 2236/00* (2013.01)

(58) Field of Classification Search
CPC ........................... A61K 31/715; A61K 36/074
See application file for complete search history.

(56) References Cited

PUBLICATIONS

Xiao et al., Arch. Pharm. Res., 2012, 35(10), p. 1793-1801.*
Sun et al., Carbohydr. Polym., 2014, 114, p. 432-439.*
Zhao et al., Carbohydr. Polym., 2010, 80, p. 783-789.*
Zhang et al., Acta Pharmacol. Sin., 2004, 25(2), p. 191-195.*
Chih-Jung Chang et al, Ganoderma lucidum reduces obesity in mice by modulating the composition of the gut microbiota, Nature Communications | 6:7489 | DOI: 10.1038/ncomms8489.

* cited by examiner

*Primary Examiner* — Jonathan S Lau
(74) *Attorney, Agent, or Firm* — WPAT, P.C., Intellectual Property Attorneys; Anthony King

(57) ABSTRACT

The present invention provides a method to prepare polysaccharides from *Ganoderma lucidum*. The prepared polysaccharides reduce body weight and fat accumulation in laboratory animals, and can therefore be used to prevent and treat obesity.

7 Claims, 9 Drawing Sheets

METHOD TO PREPARE *GANODERMA LUCIDUM* POLYSACCHARIDES POSSESSING ANTI-OBESITY PROPERTIES AND USES THEREOF

CROSS-REFERENCE TO RELATED APPLICATION

This application claims priority of Taiwan patent application No. 104116656, filed on May 25, 2015, the content of which is incorporated herein in its entirety by reference.

BACKGROUND OF THE INVENTION

1. Field of the Invention

The present invention relates to compositions and methods for preventing and treating obesity and its complications. Specifically, the invention relates to methods for preventing and treating obesity using polysaccharides isolated from *Ganoderma lucidum* as well as methods to prepare the polysaccharides.

2. The Prior Art

Obesity is considered a disease condition associated with numerous health problems and a reduced life expectancy. Growing evidence indicates that obesity is closely linked with chronic, low-grade inflammation which can lead to insulin resistance, type 2 diabetes, fatty liver disease, cardiovascular disease, obstructive sleep apnea, and cancer. The high prevalence of obesity is currently a major threat to public health, with approximately 500 million obese people and 1.4 billion overweight individuals worldwide. Prevention of obesity thus represents a major challenge for modern societies.

A number of interventions, such as calorie restriction, low-carbohydrate diets, and regular exercise, have been used to prevent and treat obesity in the general population. On the other hand, these interventions are difficult to implement on a daily basis and may be associated with low patient compliance when used over a prolonged period of time. Other treatments such as antibiotics and prebiotics are being evaluated for the management of obesity and its related metabolic disorders. For example, antibiotic treatment alters the gut microbiota, reduces blood endotoxemia, and improves glucose tolerance in genetically-modified, obese mice that lack the leptin gene (ob/ob mice) and in mice fed with a high-fat diet (HFD). In addition, prebiotics are non-digestible, fermentable polysaccharides and oligosaccharides, which reduce body weight and exert anti-inflammatory effects, mainly by enhancing the growth of specific beneficial bacteria found in the gut. Prebiotics not only alter the intestinal microbiota but also improve intestinal tight junction integrity and decrease blood endotoxemia caused by bacterial lipopolysaccharides (LPS). Prebiotics may therefore protect animals against obesity-induced inflammation.

The medicinal mushroom *Ganoderma lucidum* has a long history of use in Asian countries to promote health and longevity. Previous studies have shown that triterpenes and polysaccharides isolated from *G. lucidum* induce antidiabetic, antihyperlipidemic and antioxidant activities. Yet, it is unclear whether *G. lucidum* or any of its components may produce beneficial effects on body weight and obesity-related disorders.

In view of the growing incidence of obesity in the human population and with the difficulties observed in prevention and treatment, there is a need for alternative measures to prevent, treat and control this condition. New measures that can be introduced in the diet without necessitating considerable changes in lifestyle and without incurring in toxicity or adverse effects on health are particularly needed.

SUMMARY OF THE INVENTION

A primary objective of the present invention is to provide a method to treat obesity, comprising the administration of an effective amount of a polysaccharide isolated from *Ganoderma lucidum* to a subject, wherein the polysaccharide has a molecular weight above 135 kDa and contains at least mannose, glucose, and galactose.

According to an embodiment of the present invention, the polysaccharide further contains fucose, rhamnose, arabinose, and glucosamine.

According to an embodiment of the present invention, a weight ratio of fucose, rhamnose, arabinose, glucosamine, galactose, glucose, and mannose in the polysaccharide ranges between 2:2:2:1:16:26:47 and 3:3:3:1:17:27:48.

According to an embodiment of the present invention, the effective amount of the polysaccharide given is 0.001 mg/kg to 1,000 mg/kg per day. Preferably, the effective daily amount or dosage of *G. lucidum* polysaccharide given to a human subject (with an average weight of 70 kg) is 4.53 g (0.0646 g per kilogram of body weight).

According to an embodiment of the present invention, the polysaccharide has a molecular weight ranging from 135 kDa to 5,364 kDa, with a polydispersity index (Mw/Mn) of 6.25, and an average molecular weight of 846 kDa.

Another objective of the present invention is to provide a method to prepare the polysaccharide isolated from *G. lucidum*, comprising the following steps: extracting *G. lucidum* mycelium with water; inducing the formation of a precipitate by adding an alcohol; isolating the precipitate by centrifugation; and fractionating the precipitate to obtain a *G. lucidum* polysaccharide. Specifically, the invention provides a method comprising: (a) mixing the *G. lucidum* mycelium with water to give a first mixture, extracting the first mixture for a first predetermined time under a low-speed rotation to give a supernatant, and concentrating the supernatant to obtain a concentrated *G. lucidum* extract; (b) adding an alcohol to the concentrated *G. lucidum* extract to give a second mixture, allowing the second mixture to stand for a second predetermined time and produce a precipitate to obtain a crude *G. lucidum* polysaccharide extract; and (c) isolating the crude *G. lucidum* polysaccharide extract by centrifugation, and fractionating the crude polysaccharide extract using tangential flow filtration (TFF) to obtain a *G. lucidum* polysaccharide.

According to an embodiment of the present invention, for step (a), the *G. lucidum* mycelium is mixed with water at a ratio of 5% (w/v).

According to an embodiment of the present invention, step (a) comprises treating the mixture of *G. lucidum* and water at high temperature and mixing the mixture with a blender at a high temperature for a third predetermined time.

According to an embodiment of the present invention, step (a) comprises concentrating the water extract of *G. lucidum* using a vacuum concentrator.

According to an embodiment of the present invention, the alcohol used in step (b) is 95% ethanol.

According to an embodiment of the present invention, in step (b), 5 volumes of 95% ethanol is mixed with each volume of the concentrated *G. lucidum* water extract.

According to an embodiment of the present invention, in step (b), the second predetermined time is at least 16 hours.

According to an embodiment of the present invention, step (c) comprises fractionating the crude G. lucidum polysaccharide using TFF with a 0.2-μm hollow fiber membrane and 10 to 300-kDa cassette membranes (50 cm$^2$, polyethersulfone, PES).

The present invention provides a method for treating obesity by using a polysaccharide isolated from G. lucidum; the polysaccharide can reduce body weight and epididymal and subcutaneous fat accumulation in an obese subject. Therefore, the method of the present invention provides a new strategy to prevent and treat obesity.

BRIEF DESCRIPTION OF THE DRAWINGS

The following drawings form part of the present specification and are included here to further demonstrate some aspects of the present invention, which can be better understood by reference to one or more of these drawings, in combination with the detailed description of the embodiments presented herein.

FIG. 6A shows the effects of G1-G4 sub-fractions on body weight. FIG. 6B shows the effects of G1-G4 sub-fractions on body weight gain. FIG. 6C shows the effects of G1-G4 sub-fractions on epididymal fat levels. FIG. 6D shows the effects of G1-G4 sub-fractions on subcutaneous fat levels. Statistical analysis was performed using Student's t test (*$P<0.05$, $P<0.01$, *$P<0.001$).

DETAILED DESCRIPTION OF THE PREFERRED EMBODIMENT

In the following detailed description of the embodiments of the present invention, reference is made to the accompanying drawings, which are shown to illustrate the specific embodiments in which the present disclosure may be practiced. These embodiments are provided to enable those skilled in the art to practice the present disclosure. It is understood that other embodiments may be used and that changes can be made to the embodiments without departing from the scope of the present invention. The following description is therefore not to be considered as limiting the scope of the present invention.

Definition

The "effective amount" described in the present invention represents the amount of polysaccharide fraction isolated from Ganoderma lucidum that can reduce body weight and fat accumulation in animals and humans. The effective amount may vary depending on the organism or individual treated but can be determined experimentally using various techniques, including a dose escalation study.

As used herein, the data provided represent experimental values that can vary within a range of ±20%, preferably within ±10%, and most preferably within ±5%.

The present invention provides a method to treat obesity comprising: administering an effective amount of a polysaccharide isolated from G. lucidum to a subject considered obese. The experiments below show the effects of the isolated polysaccharides on the body weight and fat levels of mice. Generally, the G. lucidum polysaccharide of the present invention can be given to mammals and humans at a dose of 0.001-1,000 mg/kg of body weight per day. The invention is described in detail below.

Example 1

Preparation of the Polysaccharide Fraction Isolated from G. lucidum

In the present invention, the G. lucidum polysaccharides having a molecular weight above 135 kDa can effectively prevent and treat obesity, reduce body weight, and fat accumulation. The G. lucidum polysaccharide of the present invention can be added to the diet of the subject as a drug, a drink, a daily supplement, or a food, without incurring in significant lifestyle changes, toxicity or other unfavorable health conditions.

1.1 Preparation of the Concentrated Water Extract of G. lucidum

Figure 1:
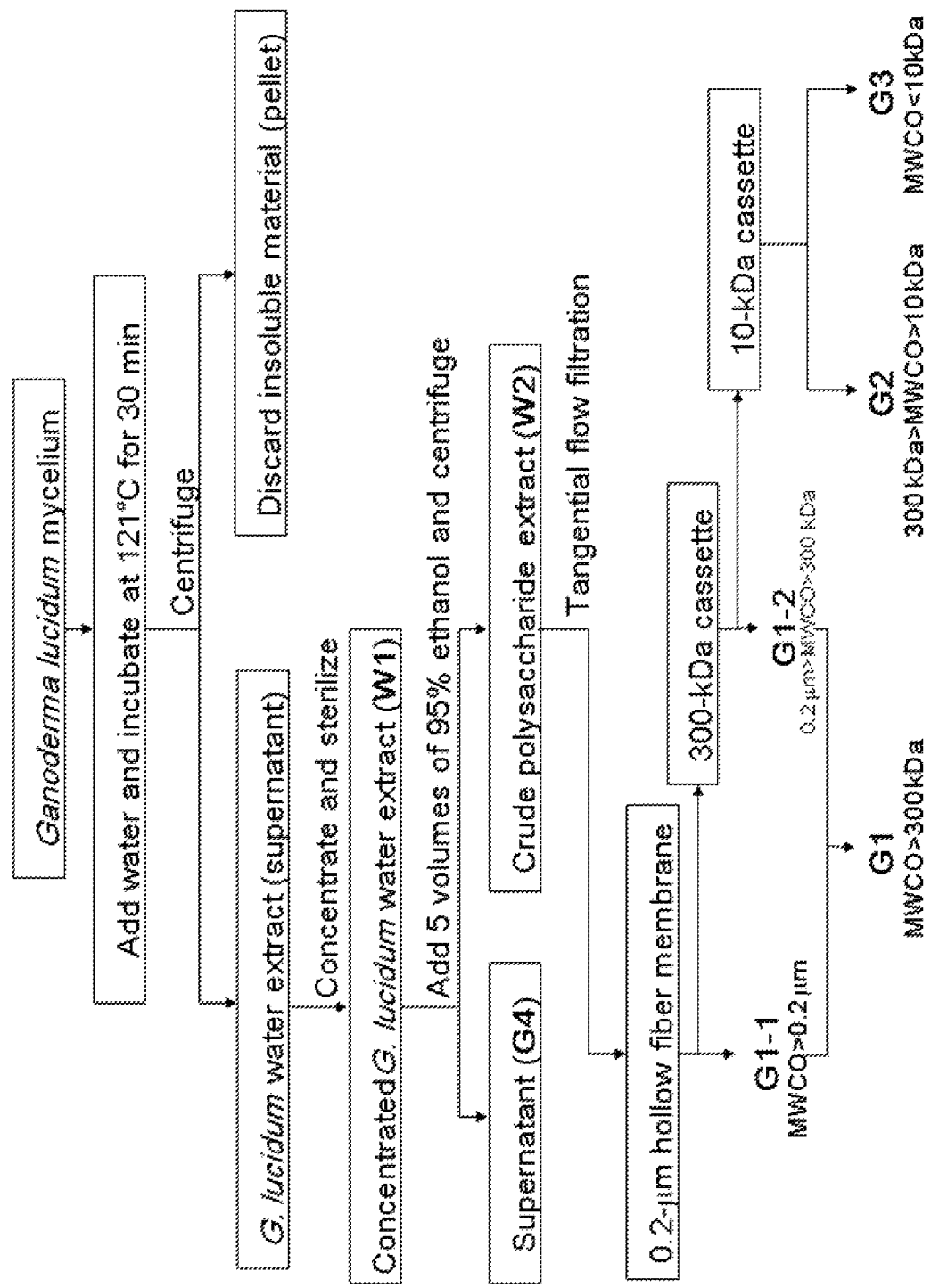
FIG. 1 shows a flowchart for the isolation of Ganoderma lucidum extracts and the G1 polysaccharide sub-fraction described in the present invention.

As shown in FIG. 1, a mixture is prepared by mixing 500 g of dried G. lucidum mycelium obtained from Chang Gung Biotechnology (Taipei, Taiwan) into 10 liters of distilled water using a 20 liter-stirred tank reactor. The 5% (w/v) mixture is agitated at a speed of 150 revolutions per minute (RPM) for 30 min at 121° C. The mixture is then centrifuged to remove insoluble material and obtain a supernatant (G. lucidum water extract). The supernatant is concentrated to a final volume of 2.5 liters using a vacuum concentrator. The concentrated supernatant is sterilized at high temperature and pressure for 20 min in an autoclave to obtain a 20% (w/v) concentrated G. lucidum water extract (labeled W1) and stored at 4° C. prior to use.

1.2 Preparation of the G. lucidum Crude Polysaccharide Extract

As shown in FIG. 1, 120 mL of 20% (w/v) the W1 concentrated G. lucidum water extract (which contains 6.03 g of total water-soluble carbohydrates; see Table 1) is mixed with 5 volumes (600 mL) of 95% ethanol and incubated at 4° C. for 16 hours to induce the precipitation of crude polysaccharide. The mixture is centrifuged to obtain a supernatant and a precipitate (pellet). The supernatant is removed, while 120 mL of 70% ice-cold ethanol is used to wash and resuspend the precipitate to obtain a mixture. The mixture is centrifuged to obtain a supernatant and a precipitate (pellet). The supernatants from three such washing-resuspension-centrifugation steps are combined to give a supernatant of 1,050 mL (labeled as G4, with total water-soluble carbohydrates of 2.82 g; see Table 1). The crude polysaccharide precipitate (pellet) is dissolved into 1,000 mL of distilled water and concentrated to a final volume of 700 mL using a vacuum concentrator in order to remove residual ethanol. Finally, distilled water is added to obtain a G. lucidum crude polysaccharide extract with a final volume of 2,400 mL (labeled as W2, with total water-soluble polysaccharides of 3.21 g; see Tables 1 and 2).

1.3 Fractionation of *G. lucidum* Crude Polysaccharide Extract 2,400 mL of *G. lucidum* crude polysaccharide extract is placed into a beaker, followed by incubation at 50° C. into a water bath. The extract is fractionated by using a tangential flow filtration (TFF) system (KrosFlo, Spectrum Laboratories) with a 0.2-μm hollow fiber membrane (1,500 cm$^2$, PES). The trans-membrane pressure (TMP) is set at 15-16 psi. 600 mL of distilled water is added into the retentate during filtration. Addition of water is repeated two times (a total of 1,800 mL distilled water is added to the retentate). A 650 mL retentate (labeled as sub-fraction G1-1, total water soluble polysaccharides of 1.26 g) and 3,600 mL of filtrate are obtained this way.

The above-mentioned 3,600 mL of 0.2-μm filtrate is placed into a beaker and incubated at 50° C. in a water bath. The 3,600 mL of filtrate is fractionated by using the TFF system with a 300-kDa cassette membrane (50 cm$^2$, PES). The TMP is set between 16-18 psi. 600 mL of distilled water is added into the retentate during filtration when the retentate ranges from 1,000 mL to 1,200 mL. A 950 mL retentate (labeled as sub-fraction G1-2, with total water soluble polysaccharides of 0.60 g) and 3,600 mL filtrate are obtained. Sub-fractions G1-1 and G1-2 are combined to obtain a final sub-fraction of 1,600 mL (labeled as sub-fraction G1; 1.86 g of total water-soluble polysaccharides; see Table 2).

The above-mentioned 3,600 mL of the 300-kDa filtrate is placed into a beaker and incubated at 50° C. in a water bath. The 300-kDa filtrate is fractioned using the TFF system with a 10-kDa cassette membrane (50 cm$^2$, PES). The TMP is set between 16-18 psi. 600 mL of distilled water is added into the retentate during filtration when the retentate ranges from 1,000 mL to 1,200 mL. The operation is repeated to obtain 970 mL of 10 kDa-to-300 kDa retentate (labeled as sub-fraction G2; 1.01 g of total water-soluble polysaccharides; see Table 2) and 3,600 mL of 10 kDa filtrate (labeled as sub-fraction G3, 0.34 g of total water-soluble polysaccharides; see Table 2).

The G1, G2, G3 and G4 sub-fractions are concentrated separately using the vacuum concentrator to obtain a final volume of 110 mL. Concentrated sub-fractions are sterilized at high temperature and pressure for 20 min in an autoclave and stored at 4° C. prior to use.

1.4 Total Water-Soluble Carbohydrate and Polysaccharide Content of the Isolated *G. lucidum* Extracts and Sub-Fractions The phenol-sulfuric acid assay is used to determine the level of total water-soluble carbohydrates and polysaccharides found in the isolated *G. lucidum* extracts and polysaccharide sub-fractions, which include 20% (w/v) the concentrated *G. lucidum* water extract (labeled as W1, 120 mL), the *G. lucidum* crude polysaccharide extract (labeled as W2, 2400 mL), a combination of the retentate of the 0.2-μm hollow fiber step and the 300-kDa-cutoff pore membranes (labeled as G1 sub-fraction; 1,600 mL), the retentate of the 10 kDa cassette membrane (labeled as G2 sub-fraction; 970 mL), the filtrate of the 10-kDa-cutoff pore membranes (labeled as G3 sub-fraction; 3,600 mL), and the supernatants of the 95% ethanol precipitation and wash process (labeled as G4 sub-fraction; 1,050 mL). To establish a standard curve for the phenol-sulfuric acid assay, glucose standard solutions are prepared at 0, 0.02, 0.04, 0.06, 0.08, 0.10, 0.12, 0.14, 0.16, 0.18, and 0.20 mg/mL. 200 μL of each solution is placed into 1.5-mL tubes. 200 μL of 5% phenol is added and the solution is mixed. 1 mL of sulfuric acid is added and the solution is mixed. After incubation for 20 min, absorbance is monitored using a spectrophotometer at 490 nm to obtain the calibration curve of glucose standard solutions. The calculated R squared is higher than 0.99. The sample solutions are appropriately diluted and 200 μL of each diluted sample solution is placed into 1.5-mL tubes. Phenol and sulfuric acid are added as described above. After incubation for 20 min, the absorbance is monitored and the value obtained is plotted into the calibration curve of glucose standard solution to determine the concentration of total water-soluble carbohydrates or total water-soluble polysaccharides of the samples.

Total water-soluble carbohydrates and polysaccharides found in the extracts and polysaccharide sub-fractions isolated from *G. lucidum* are shown in Table 1 and 2. Table 1 and 2 show that the W2 crude polysaccharide extract isolated from *G. lucidum* contains 3.21 g of water-soluble polysaccharides and that the G1 sub-fraction contains 1.86 g of polysaccharides with a molecular weight above 300 kDa, which accounts for 57.9% of the total polysaccharides found in the crude polysaccharide extract (W2).

TABLE 1

Water-soluble carbohydrates and polysaccharides in the isolated *G. lucidum* extracts

| Fraction | | Content (g) | Percentage (%) |
|---|---|---|---|
| W1 | Total water-soluble carbohydrates | 6.03 | 100 |
| W2 | Total water-soluble polysaccharides | 3.21 | 53.2 |
| G4 | Mono-, di-, oligo-saccharides | 2.82 | 46.8 |

TABLE 2

Polysaccharide distribution of the *G. lucidum* crude polysaccharide extract (W2)

| Fraction | | Content (g) | Percentage (%) |
|---|---|---|---|
| W2 | Total water-soluble carbohydrates | 3.21 | 100 |
| G1 | MWCO >300 kDa | 1.86 | 57.9 |
| G2 | 300 kDa > MWCO > 10 kDa | 1.01 | 31.5 |
| G3 | 10 kDa > MWCO | 0.34 | 10.6 |

MWCO: molecular weight cut-off 1.5 Monosaccharide Analysis of G1 Polysaccharide Sub-Fraction Isolated from *G. lucidum*

High pH anion exchange chromatography-pulsed amperometric detection (HPAEC-PAD) is used to analyze the monosaccharide components of the G1 sub-fraction. Standard monosaccharide solutions of L-fucose, L-rhamnose, D-galactosamine, D-arabinose, D-glucosamine, D-galactose, D-glucose and D-mannose are prepared at concentrations of 0.1, 0.5, 1, 2, and 5 mg/L. 25 μL of each solution is used for ionic chromatography analysis with the HPAEC-PAD Dionex ICS-5000 System (CarboPacPA1 column with an internal diameter of 4×250 mm, Thermo Scientific). Elution is performed with 16 mM NaOH (which represents a mixture of water and 200 mM NaOH at the volume ratio of 92:8). The flow rate is set at 1 mL/min. The column oven is set at a temperature of 30° C. After 30 min, the peak areas of each monosaccharide standard are determined at 0.1, 0.5, 1, 2, and 5 mg/L. The standard curve of the seven monosaccharide standards is established (calculated $R^2$>0.99).

Figure 2:
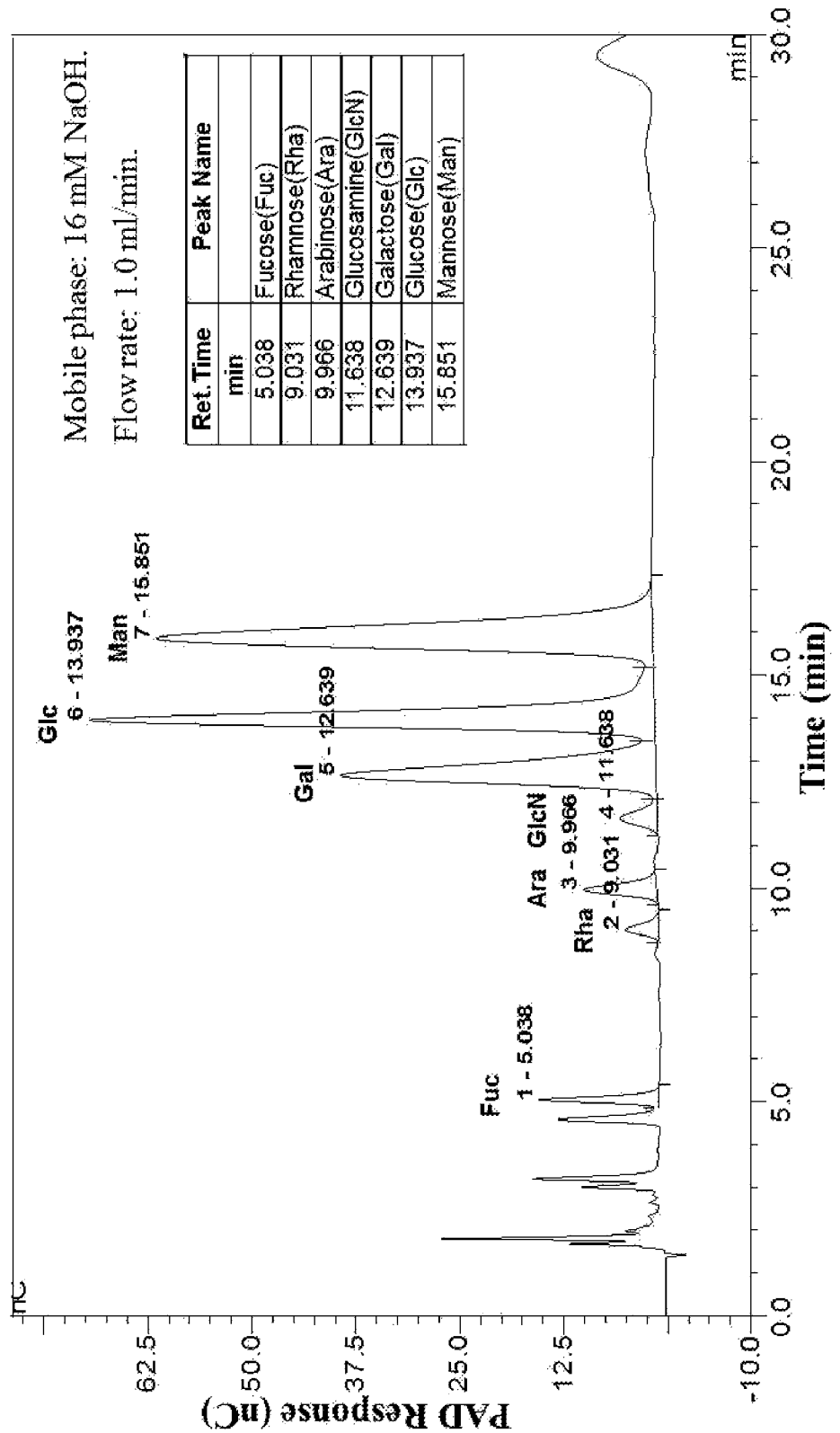
FIG. 2 shows the monosaccharide analysis of G. lucidum polysaccharide sub-fraction G1 of the present invention; the analysis was performed using high-performance anion exchange chromatography with pulsed amperometric detection (HPAEC-PAD).

0.21 mL of G1 sub-fraction (3 mg of total water-soluble polysaccharides) is hydrolyzed with 2.79 mL of distilled water and 1.33 mL trifluoroacetic acid at 112° C. in a sealed tube for 12 hours. The acid is removed by co-distillation with water after hydrolysis is completed. Each hydrolysate (1 mg) is dissolved in pure water (1 mg/mL). After a 4-fold dilution of the hydrolysate with pure water (0.25 mg/mL), 25 μL of the hydrolysate solution is used for ionic chromatography analysis by HPAEC-PAD analysis. Elution is performed with 16 mM NaOH as above. After 30 min of analysis, the analytic HPAEC-PAD profile of the hydrolysate solution is acquired. The monosaccharide component and molar ratio of the G1 fraction is determined by comparison with the standard curve. The G1 sub-fraction consists of 2.8% fucose, 2.5% rhamnose, 2.9% arabinose, 1.1% glucosamine, 16.9% galactose, 26.3% glucose, and 47.5% mannose (Table 3 and 4 and FIG. 2).

TABLE 3

Monosaccharide analysis of the G1 polysaccharide sub-fraction using HPAEC-PAD

| Monosaccharide | Percentage (%) |
| --- | --- |
| Fucose | 2.8 |
| Rhamnose | 2.5 |
| Arabinose | 2.9 |
| Glucosamine | 1.1 |
| Galactose | 16.9 |
| Glucose | 26.3 |
| Mannose | 47.5 |

TABLE 4

Monosaccharide molar ratio of the G1 polysaccharide sub-fraction

| Monosaccharide | Molar ratio |
| --- | --- |
| Fucose | 0.07 |
| Rhamnose | 0.06 |
| Arabinose | 0.07 |
| Glucosamine | 0.02 |
| Galactose | 0.36 |
| Glucose | 0.55 |
| Mannose | 1 |

1.6 Molecular Weight Distribution of the G1 Polysaccharide Sub-Fraction Isolated from *G. lucidum*

The molecular weight of the isolated G1 polysaccharide sub-fraction is analyzed using size-exclusion chromatography (SEC) and high performance liquid chromatography with refractive index (RI), differential viscosity (DV) and light scattering (LS) detectors (with a refractive index detector, Waters model 2410, and a Viscotek 270 dual detector). Dextran 670 (667,800 Da) at 1.5 mg/mL is used as a standard marker to calibrate the system. 100 μL of sample is analyzed on two connected GPC columns (TSKgel G5000PWxL and TSKgel G6000PWxL; 7.8×300 mm) Elution is performed with 0.02% $NaNO_3$ in pure water and the flow rate is set at 0.8 mL/min (column temperature of 22° C.).

Molecular weight analysis of the G1 polysaccharide sub-fraction (total water-soluble polysaccharide of 7.5 mg/mL) is calculated using the OmniSEC software (Viscotek) and the following equations:

Mn: number average molecular weight $$Mn = \frac{\Sigma NiMi}{\Sigma Ni}$$

Mw: weight average molecular weight $$Mw = \frac{\Sigma NiMi^2}{\Sigma NiMi}$$

Mz: higher average molecular weight $$Mz = \frac{\Sigma NiMi^3}{\Sigma NiMi^2}$$

Figure 3:
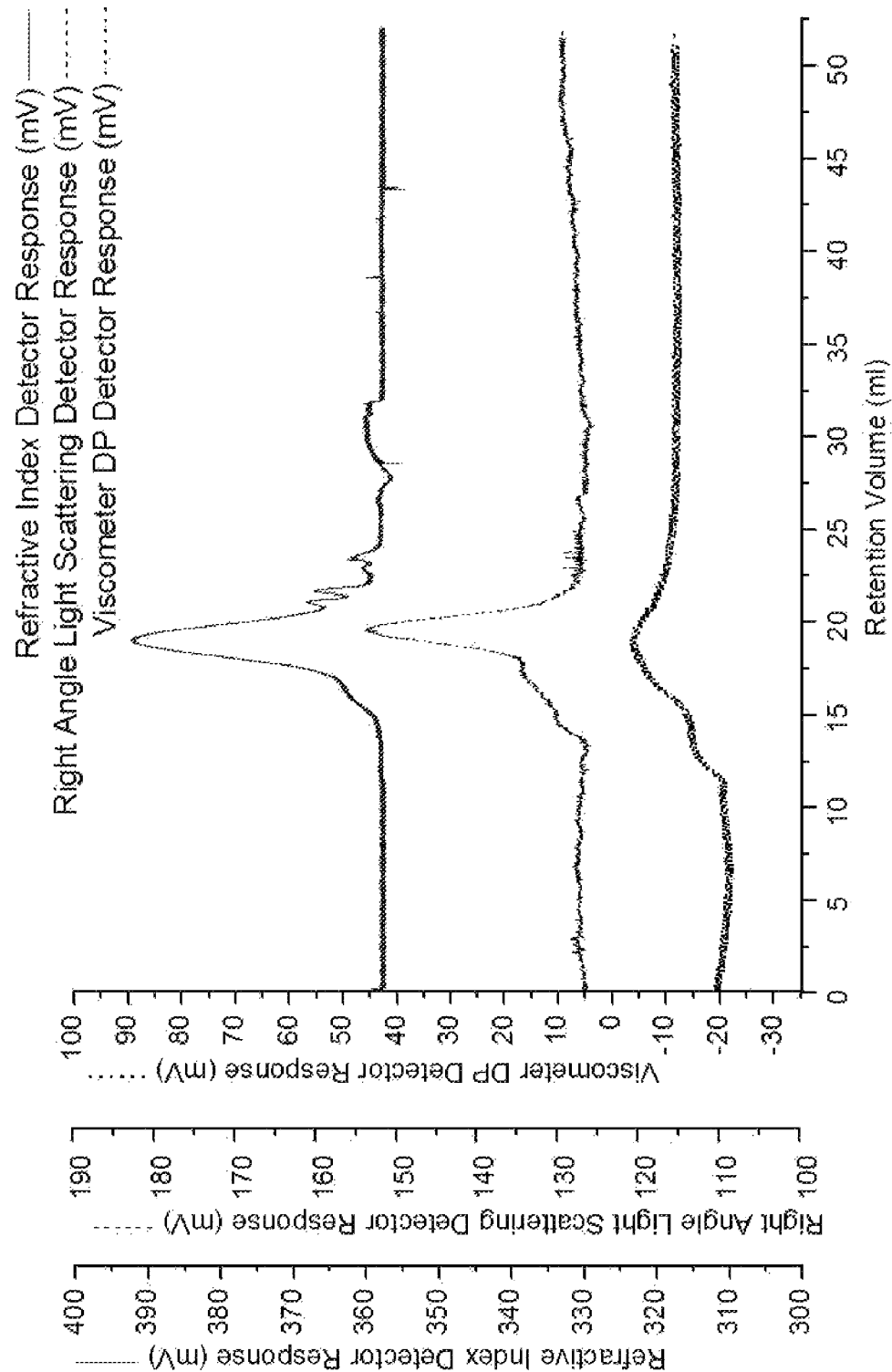
FIG. 3 shows the gel permeation chromatogram of G. lucidum polysaccharide sub-fraction G1 of the present invention.
Figure 4:
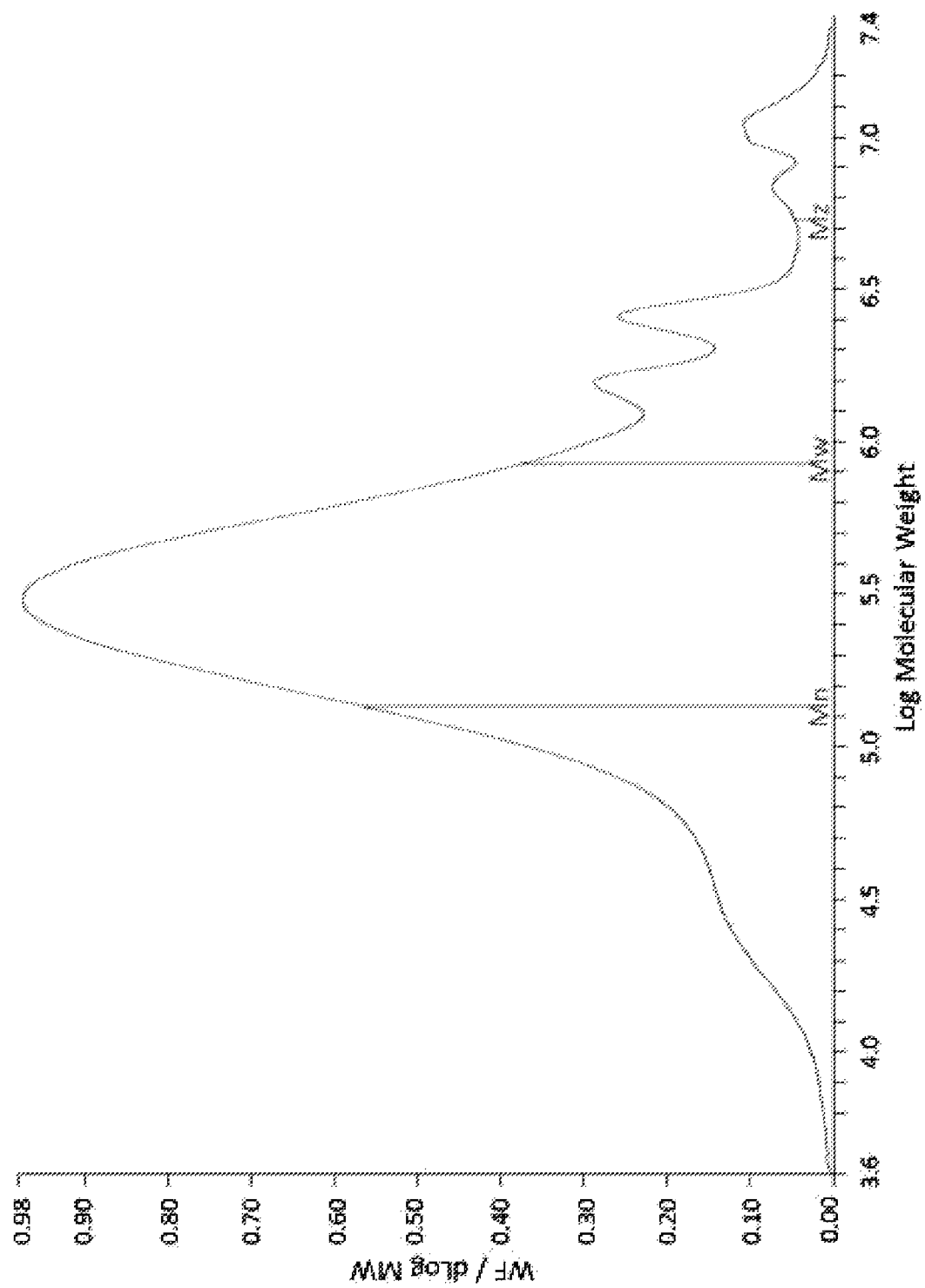
FIG. 4 shows the graph of weight fraction (WF)/dLog molecular weight (MW) vs. log molecular weight (MW) of G. lucidum polysaccharide sub-fraction G1 of the present invention.
Figure 5:
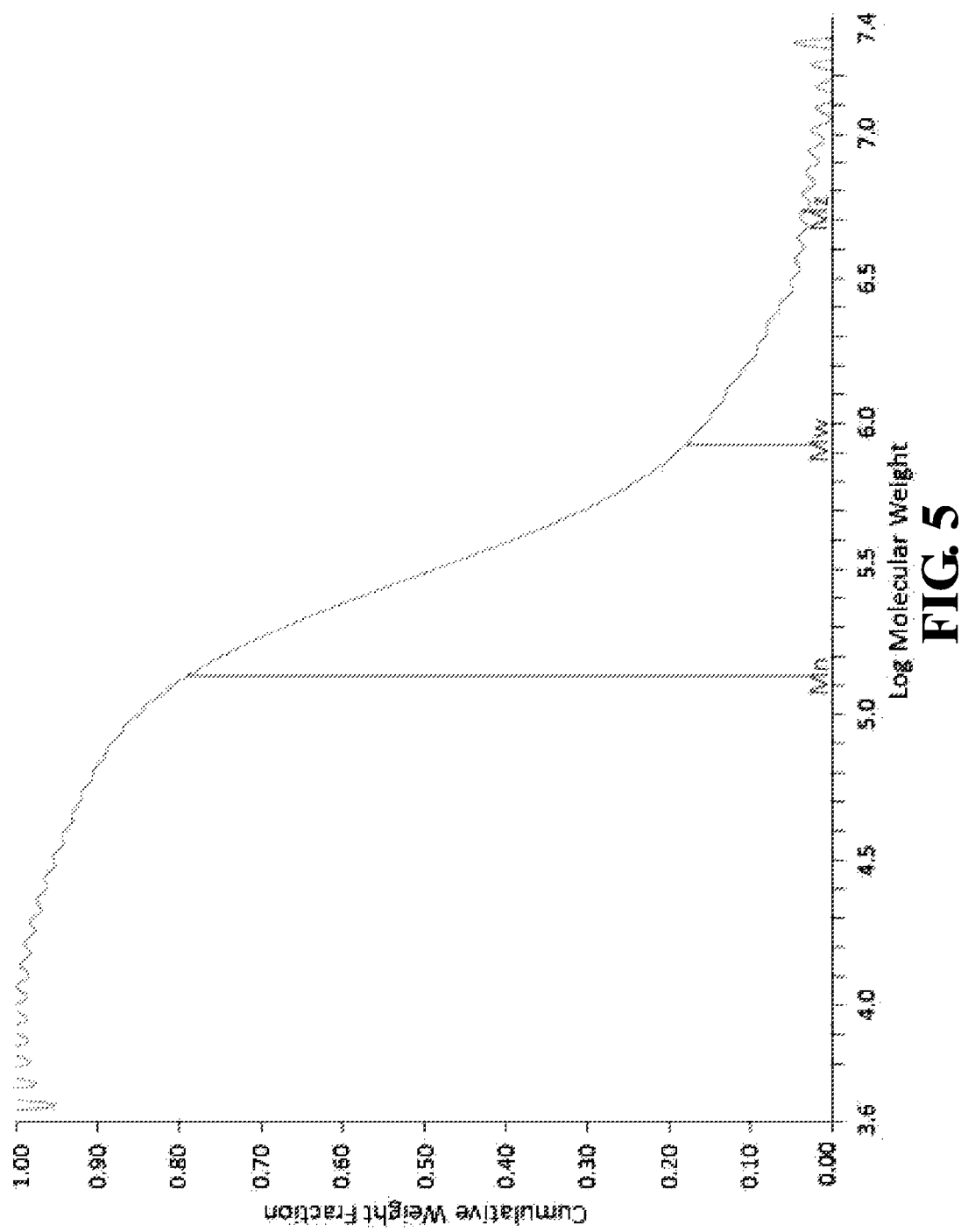
FIG. 5 shows the graph of the cumulative weight fraction vs. log MW of G. lucidum polysaccharide sub-fraction G1 of the present invention.
Figure 6A:
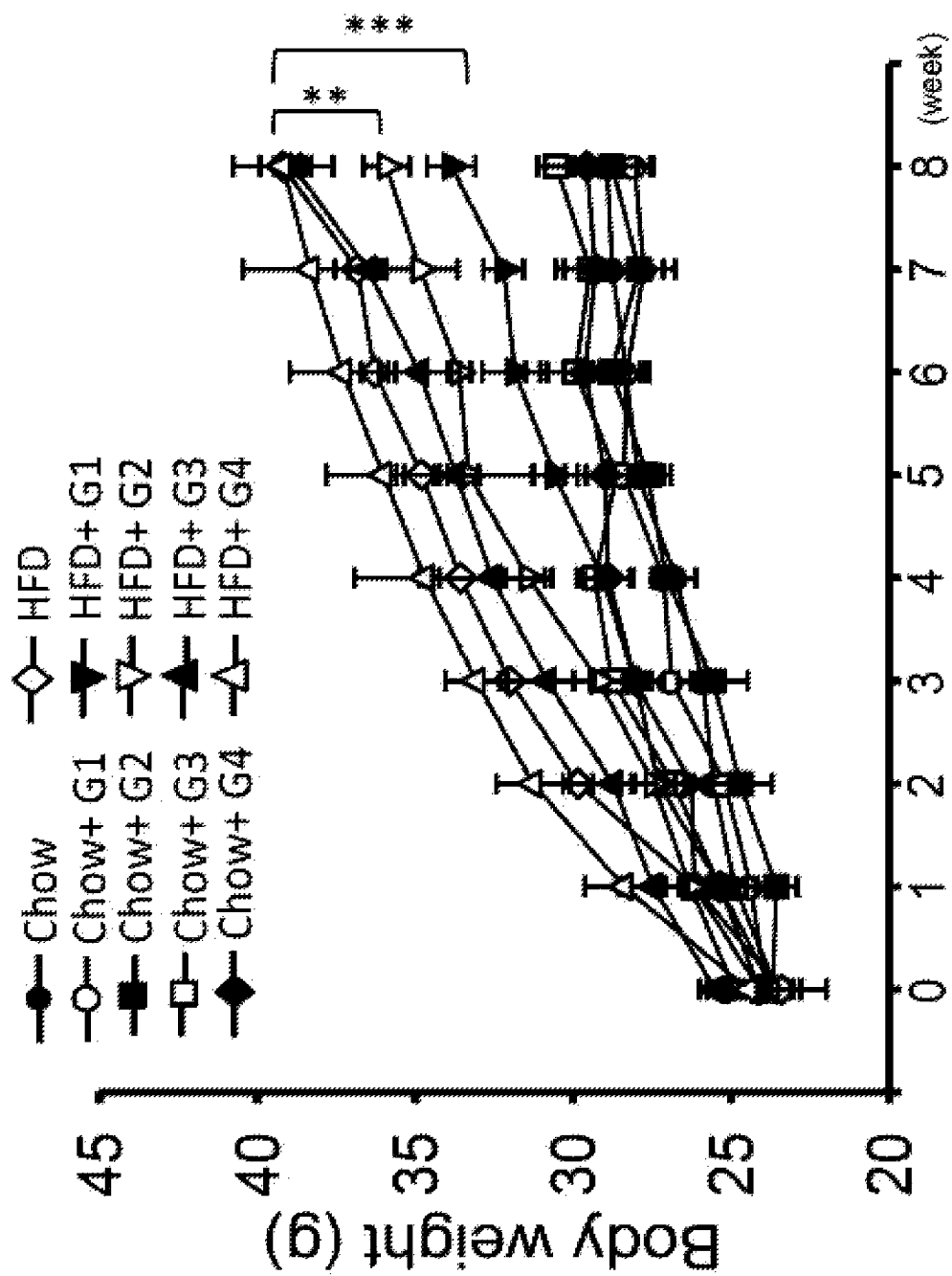
FIGS. 6A to 6D show the anti-obesity effects of G. lucidum polysaccharide sub-fractions (G1-G4) of the present invention on mice fed with either standard chow or a high-fat diet (HFD).
Figure 6B:
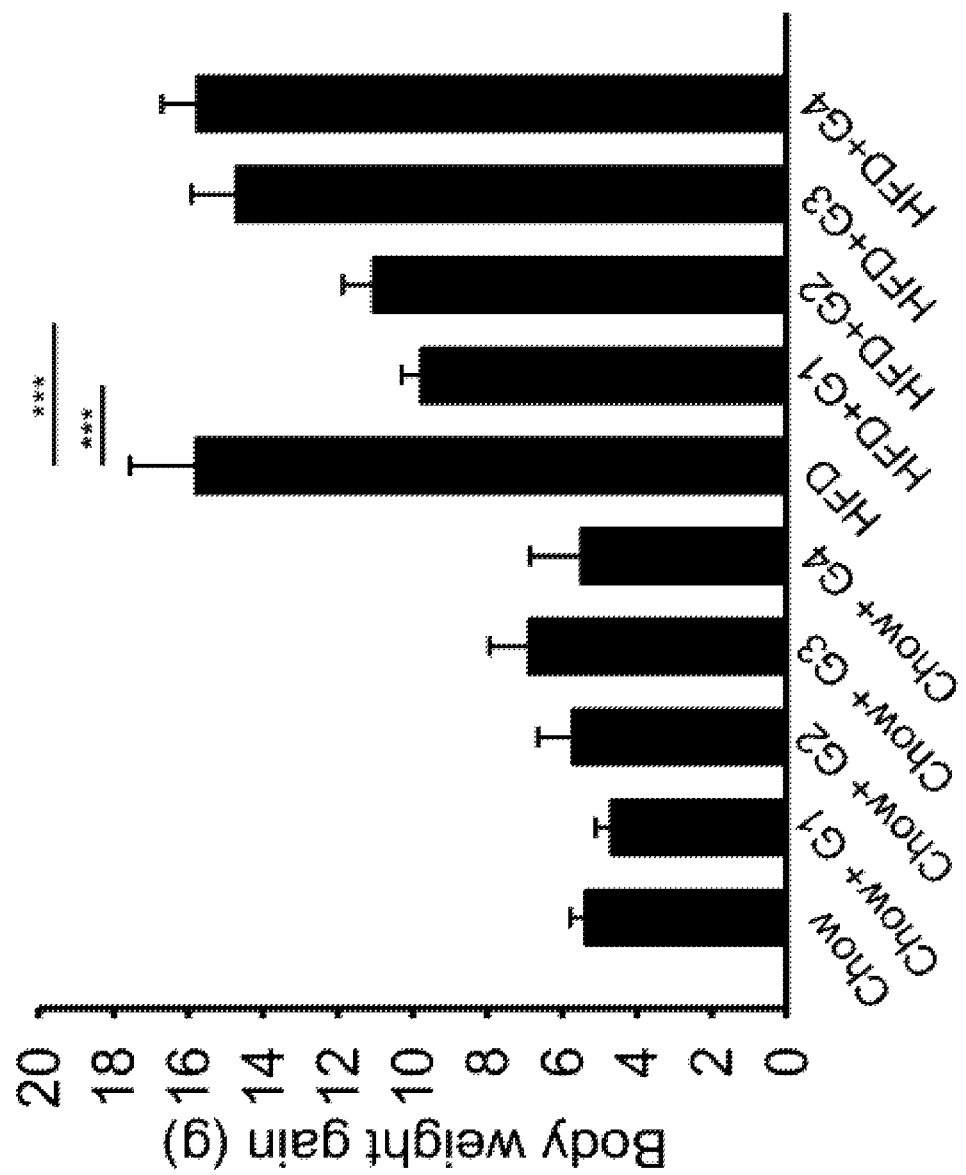
Figure 6C:
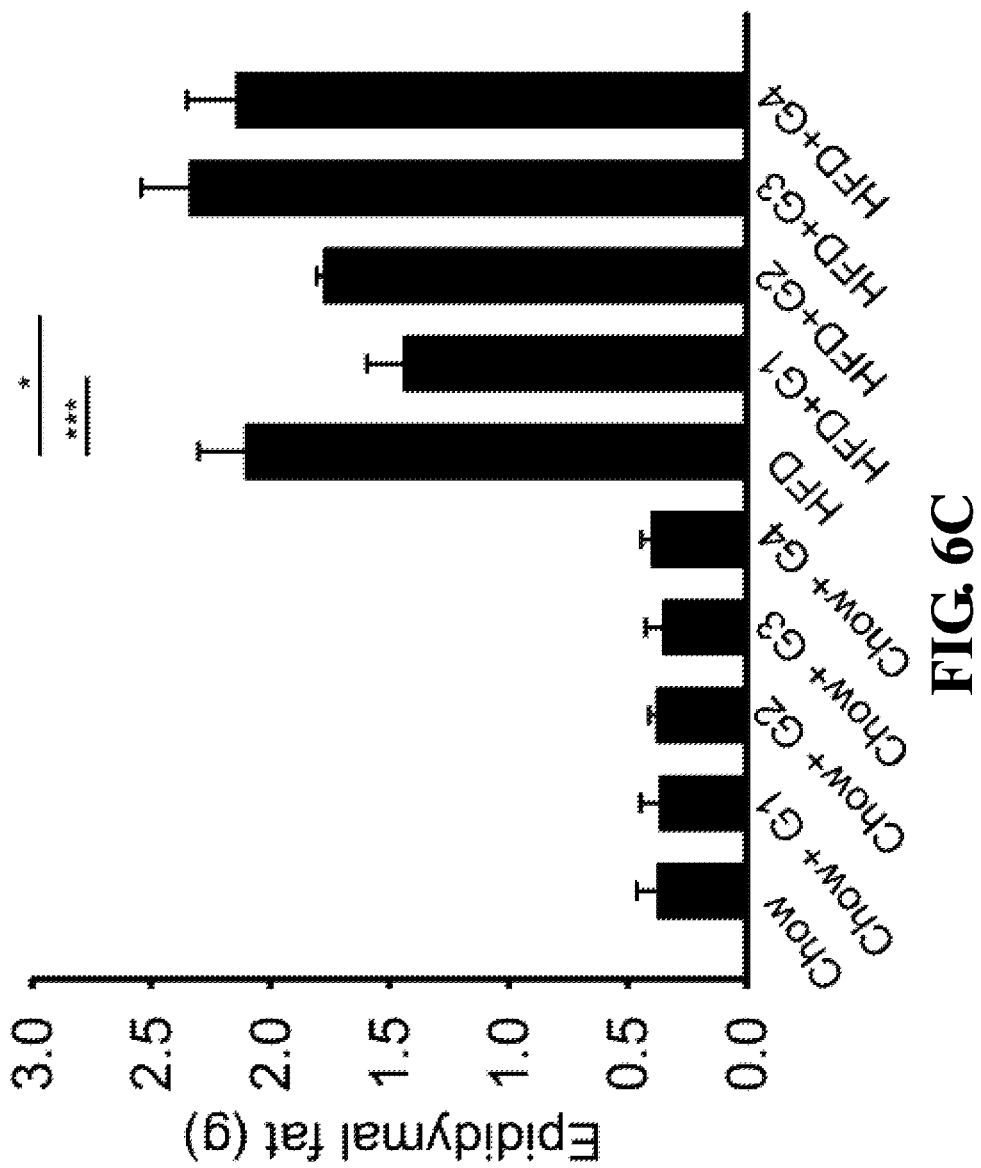
Figure 6D:
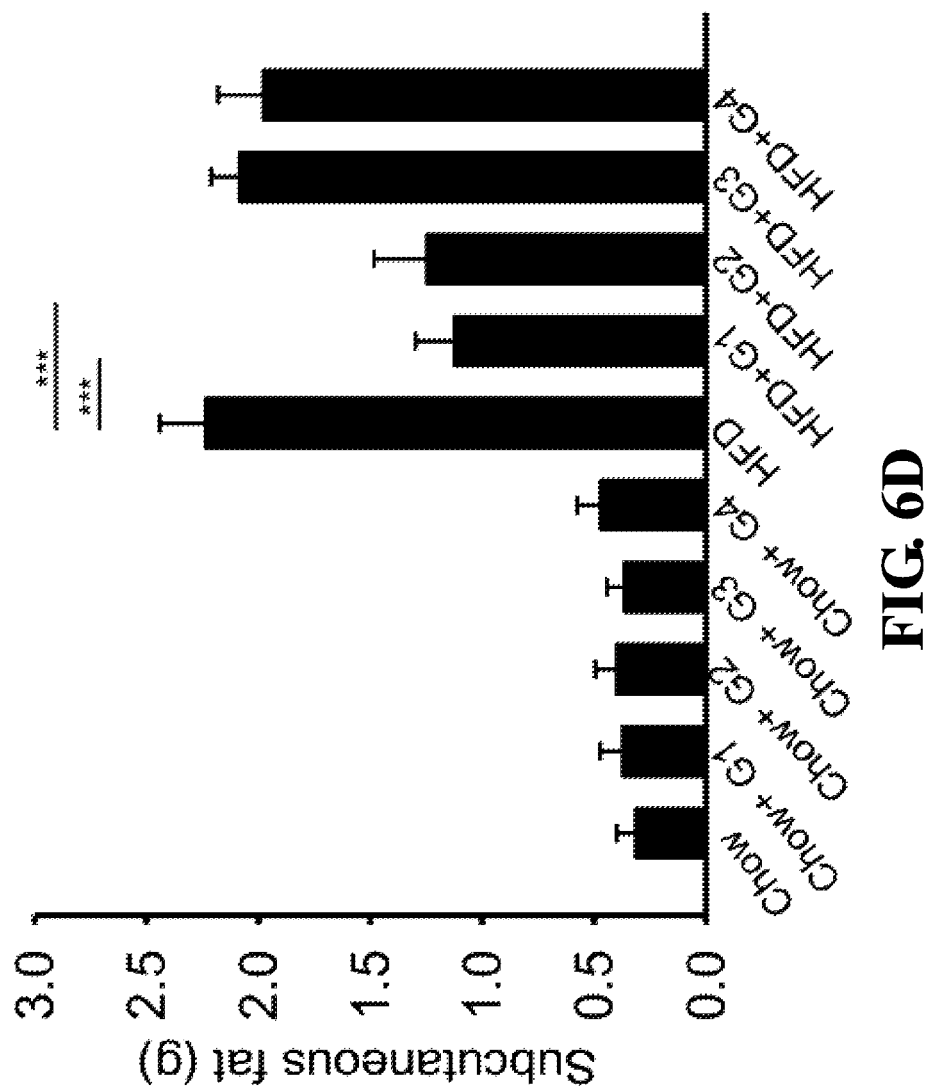

Mp: molecular weight at peak maximum, which is measured at the point of the molecular weight distribution maximum
Mi: molecular weight of a chain
Ni: number of chains of that molecular weight Based on RI-DV-LS analysis of the G1 sub-fraction (FIG. 3), the molecular weight distribution of this sub-fraction is determined (FIG. 4). Based on these experimental data, the following parameters are calculated: Mn (number average molecular weight), 135,395 Da; Mw (weight average molecular weight), 846,622 Da; Mz (higher average molecular weight), 5,364,000 Da; and Mp (molecular weight at peak maximum), 309,436 Da. The cumulative weight fraction is determined (FIG. 5). Based on these data (FIG. 5), the cumulative weight fraction values of Mn and Mw are 0.79 and 0.18, corresponding to molecular weights of 135,395 Da (Mn) and 846,622 Da (Mw), and a polydispersity index (Mw/Mn) of 6.25, which represents approximately 61% of the total polysaccharide weight.

Even though the G1 polysaccharide sub-fraction isolated from *G. lucidum* represents a retentate obtained with a 300-kDa cut-off membrane, biopolymers such as polysaccharides are known to aggregate under these conditions, an observation which may explain why the calculated molecular weight of the polysaccharides found in the G1 sub-fraction is lower than the molecular weight cut-off of the membranes used to isolate this sub-fraction. Based on the information derived from FIG. 4, the cumulative weight fraction of the G1 sub-fraction described in the present invention has a molecular weight above 135 kDa.

Example 2

Effects of the Isolated *G. lucidum* Polysaccharide Sub-Fractions on Body Weight and Fat Accumulation in HFD-Fed Mice In the present invention, C57BL/6NCrlBltw mice are fed with standard chow (13.5% of energy from fat) in the control group (Chow) or with HFD (60% of energy from fat) in the experimental group. The mice are also treated daily with 100 μL of polysaccharide sub-fraction (G1, G2, G3, or G4) or distilled water by intragastric gavage for two months (n=5 mice for each group). The animal groups consist of HFD+G1, HFD+G2, HFD+G3, HFD+G4, HFD, Chow+G1, Chow+G2, Chow+G3, Chow+G4, and Chow.

FIG. 6 shows the effects of the *G. lucidum* polysaccharide sub-fractions isolated in the present invention on the body weight and fat levels of chow- and HFD-fed mice. Feeding with the HFD increased body weight, weight gain, and fat levels compared to feeding with chow (FIG. 6A-D). Notably, the HFD+G1 group showed statistically significant reductions of body weight (FIG. 6A), weight gain (FIG. 6B), epididymal fat (FIG. 6C), and subcutaneous fat (FIG. 6D) compared to HFD mice. While the HFD+G2 group also showed statistically significant anti-obesity effects compared to the HFD group, the anti-obesity effects produced by the G1 sub-fractions were more pronounced than the effects produced by G2 or other sub-fractions (FIG. 6A-D). These results show that the *G. lucidum* polysaccharides with a molecular weight above 135 kDa (G1 sub-fraction) produce the most significant anti-obesity effects in obese animals.

As seen in FIG. 6, *G. lucidum* polysaccharide sub-fraction G1 can reduce body weight (FIG. 6A), weight gain (FIG. 6B), and fat levels (FIGS. 6C and D) in HFD-fed mice. Given that the polysaccharide content of sub-fraction G1 is 1.94 g/100 mL, the effective daily amount or dosage of *G. lucidum* polysaccharide required to produce anti-obesity effects in mice (with an average weight of 30 g) is 0.0019 g/mouse (for a period of two months). Accordingly, the effective daily amount or dosage of *G. lucidum* polysaccharide sub-fraction G1 that would produce similar anti-obesity effects in a human subject (with an average weight of 70 kg) is estimated at 4.53 g/individual, which is equal to 0.0646 g/kg.

The present invention provides a method for treating obesity using *G. lucidum* polysaccharides, as well as a method to prepare the *G. lucidum* polysaccharides having anti-obesity properties. The *G. lucidum* polysaccharides of the present invention can reduce body weight and fat accumulation in animals and humans. Accordingly, the present invention provides a new strategy to reduce obesity and induce weight loss in humans. This strategy has obvious potential commercial applications given the vast amount of products and treatments available on the market to reduce body weight or maintain an optimal weight and general health. Although the present invention has been described with reference to the preferred embodiments, it will be apparent to those skilled in the art that a variety of modifications and changes in form and detail may be made without departing from the scope of the present invention defined by the appended claims.

What is claimed is:

1. A method for treating obesity, the method comprising administering an effective amount of a polysaccharide isolated from *Ganoderma lucidum* mycelium to a subject in need thereof, wherein the polysaccharide has a molecular weight above 135 kDa and contains at least mannose, glucose, and galactose;
    wherein treating obesity consists of reducing body weight and body weight gain.

2. The method according to claim 1, wherein the polysaccharide further contains fucose, rhamnose, arabinose, and glucosamine.

3. The method according to claim 2, wherein a weight ratio of the fucose, rhamnose, arabinose, glucosamine, galactose, glucose, and mannose in the polysaccharide ranges between 2:2:2:1:16:26:47 and 3:3:3:1:17:27:48.

4. The method according to claim 1, wherein the effective amount of the polysaccharide given is from 0.001 mg/kg to 1,000 mg/kg per day.

5. The method of claim 1, wherein the effective amount of the polysaccharide is 0.0646 g per kilogram of body weight.

6. The method according to claim 1, wherein the molecular weight of the polysaccharide ranges from 135 kDa to 5,364 kDa, with a polydispersity index (Mw/Mn) of 6.25.

7. The method according to claim 1, wherein the average molecular weight of the polysaccharide is 846 kDa.

* * * * *